United States Patent [19]

Moseley

[11] Patent Number: 5,001,763
[45] Date of Patent: Mar. 19, 1991

[54] ELECTROACOUSTIC DEVICE FOR HEARING NEEDS INCLUDING NOISE CANCELLATION

[75] Inventor: William T. Moseley, Shreveport, La.

[73] Assignee: MNC Inc., Shreveport, La.

[21] Appl. No.: 392,264

[22] Filed: Aug. 10, 1989

[51] Int. Cl.$^5$ ............................................. G10K 11/16
[52] U.S. Cl. ........................................ 381/71; 381/72
[58] Field of Search ..................... 381/150, 163, 71, 72

[56] References Cited

U.S. PATENT DOCUMENTS

| | | | |
|---|---|---|---|
| 3,009,991 | 11/1961 | Beckey . | |
| 3,278,695 | 10/1966 | Craig et al. | 381/163 |
| 3,562,429 | 2/1971 | West . | |
| 3,890,474 | 6/1975 | Glicksberg | 281/72 |
| 3,922,488 | 11/1975 | Gabr . | |
| 3,952,158 | 4/1976 | Kyle et al. | 381/72 |
| 4,025,724 | 5/1977 | Davidson, Jr. et al. . | |
| 4,195,360 | 3/1980 | Fothergill . | |
| 4,455,675 | 6/1984 | Bose . | |
| 4,504,703 | 3/1985 | Schneiter et al. | 381/163 |
| 4,644,581 | 2/1987 | Sapiejewski . | |
| 4,654,871 | 3/1987 | Chaplin et al. | 381/72 |
| 4,677,677 | 6/1986 | Eriksson . | |
| 4,833,719 | 5/1989 | Carme et al. | 381/72 |

FOREIGN PATENT DOCUMENTS

| | | |
|---|---|---|
| 212840 | 3/1987 | European Pat. Off. . |
| 2925134 | 1/1981 | Fed. Rep. of Germany . |
| 2172769 | 9/1986 | United Kingdom . |

OTHER PUBLICATIONS

John Free, "Noise Zapper", Popular Science, Jan. 1987, pp. 76, 77, 96.

Primary Examiner—Forester W. Isen
Attorney, Agent, or Firm—Cushman, Darby & Cushman

[57] ABSTRACT

A device for performing electroacoustic functions including noise cancellation, hearing aid, communication interface, headset, feed for recording device, and headphone functions. The device includes composite transducers connected to a control unit. The composite transducers can be mounted on a headband and are configured to include input transducers for converting acoustic waves into electrical signals for processing by a control unit, and output transducers for converting the processed electrical signals to processed sound waves. The control unit includes an inverter/amplifier and a mixer/output amplifier for inverting the electrical input and controlling the gain for either adjusting the gain to maximize a noise cancellation function or increasing the gain beyond the minimum level heard by the ear to a desired level for a hearing aid function. Connectors for connecting recorders and a boom microphone, and function selection switches are provided by the control means for connecting circuit components of the control unit selectively for performing the above functions. The input and output transducers have oppositely oriented diaphragms mounted in a common plane to provide an inverted acoustic wave in real time for combining with and substantially cancelling an incoming acoustic wave.

29 Claims, 6 Drawing Sheets

ELECTROACOUSTIC DEVICE FOR HEARING NEEDS INCLUDING NOISE CANCELLATION

This invention relates to electroacoustic devices and more particularly to an improved electroacoustic apparatus which provides useful tools for the human ear and its hearing needs including audio noise cancellation, sound level amplification, and interfaces for communication devices.

BACKGROUND OF THE INVENTION

Electroacoustic devices have included electronic audio noise cancelling devices for the attenuation of broadband noise at the ear. Such devices are either passive devices or active devices Passive devices have generally comprised rigid cups lined with acoustically absorbent material. The cups are edged with cushions to enclose the ears in substantially air tight cavities lined with the acoustically absorbent material.

Active devices for noise cancellation have included microphones, amplifiers and loud speakers to measure noises in local areas relatively distant from the sources and to produce equal amplitude and opposite phase acoustic signals to cancel out the sound in the areas. Such known arrangements are prone to produce interference patterns which even increase the noise intensity in other locations.

In one noise cancelling apparatus an array of independent sound cancellation units is arranged over a vibrating noise generating surface. Each unit includes an arrangement of acoustic transducers positioned adjacent the surface to obtain an electrical average of the local acoustic noise generated by a predetermined zone of the surface. The electrical sum average is changed in phase and gain by an active filter whose output drives an acoustic projector also positioned adjacent the surface. The acoustic output sums with the original noise signal in the acoustic far field, thus tending to cancel the noise. In essence, each vibrating surface zone and its associated sound cancellation unit tend to form an acoustic doublet. A signal indicative of the projector output is used as a feedback signal, with appropriate time delays to cancel the effect of the projected output signal being picked up by the unit's transducer, and to cancel the effect of the output of other projectors of the array. Those persons skilled in the art desiring more information concerning this system are referred to U.S. Pat. No. 4,025,724 issued May 24, 1977 to Davisson, Jr. et al.

In another electronic audio noise cancelling device, a microphone is disposed on the outside of an earphone relative to the auditory canal within an ear. An amplifier processing circuit has an input connected to the microphone. The circuit includes a filter channel and an operational amplifier channel. The filter channel includes an active filter and a variable gain amplifier and the operational amplifier channel includes an operational amplifier and a variable gain amplifier. The two variable gain amplifiers are complementary.

The two channels are combined with the summed signal being fed through a user adjustable variable gain amplifier to a summing circuit. At the summing circuit a signal on a communication channel is introduced. The summing circuit output is fed to the earphone 12.

The amplifier processing circuitry provides for user adjustment of phase and amplification to enable a preferred cancellation signal to be developed to the earphone. The output provides unwanted noise cancellation at the earphone. Those persons having a need for more information concerning the device are referred to UK Patent Application GB 2172769A, published Sept. 24, 1986 for an Ear Defender.

The problems with the above devices stem from acoustic time delay and the use of active filters. In acoustic time delay the distance between the microphone and loudspeaker has a phase shift associated with it; thereby allowing only certain frequencies to be 180 degrees out of phase. In an active filter also, only some frequencies can be made 180 degrees out of phase. Signals that are out of phase by 180 degrees will cancel, but the addition of the phase response of the filter makes for a random response depending on the setting of the filter and the distance between the microphone and loud speaker. An additional problem with the arrangement having a loud speaker downstream of the microphone is that if the speed of sound changes, the frequencies being cancelled also change. Another problem also exists when the microphone is separated from the loud speaker in that a path is created for reflections to enter the ear that are not processed.

Miniature portable sound amplifiers for persons with impaired hearing are well known as hearing aids. A hearing aid includes a microphone, audio amplifier, earphone, and batteries.

SUMMARY OF THE INVENTION

In accordance with the present invention, an apparatus is provided with features as follows:

1. The apparatus reduces the sound level to the ear for improved audible noise reduction;
2. The apparatus is capable of performing a hearing aid function such as amplifying the sound level to the ear;
3. The apparatus provides a communication interface for inputting special signals such as dispatched or emergency communications and providing a signal output from a boom microphone;
4. The apparatus provides an amplified headset which can be used with personal entertainment equipment or where other amplified signals are required to drive a miniature type headset;
5 The apparatus provides a signal source to feed personal or professional recording devices such as mono or binaural microphone sources; and
6. The apparatus provides a normal open air ultralight headphone for use in anyway that this type of headphone may normally be used.

Accordingly it is an object of the present invention to provide an electroacoustic apparatus having improved capabilities to meet the needs of human ears.

Another object of the invention is to provide a multifunction electroacoustic apparatus configured to reduce substantially the circuitry required to perform its functions.

Yet another object of the invention is to provide a multifunction electroacoustic apparatus that minimizes the effect of temperature, humidity, and barometric pressure which change the speed of sound and would change the acoustic time delay and the frequencies that would have been out of phase 180 degrees.

Still another object of the invention is to provide a multifunction electroacoustic apparatus which may receive an acoustic signal and output a processed acoustic signal in the same time domain.

A further object of the invention is to provide a multifunction electroacoustic apparatus having many applications including: noise reduction; noise reduction accompanied by an auxiliary input, and interfacing user circuits connected thereto via access points.

Briefly stated the multifunction electroacoustic apparatus, which constitutes the subject matter of the invention hereinafter described in detail and provides useful tools for the human ear and its needs, includes a control unit and at least one composite transducer which might be attached to a headband and connected to the control unit. The control unit provides function selection and the signal processing for the selected function.

The control unit is made small enough to fit into a pocket, worn on a belt, clipped to an apparel suitable to support the unit, or made to fit a variety of other size chassis.

Each composite transducer includes two independent electroacoustic transducers. Depending on the application, the first may be an input transducer for converting sound waves to electric waves, and the second may be an output transducer for converting audio frequency electric waves into acoustic waves. The transducers are thus mounted so that their diaphragms are oriented in opposite directions, with one transducer mounted in the middle of the other, and both diaphragms aligned in the same plane. In other applications, hereinafter described, the above mentioned output transducer may be used as an input transducer and if the above mentioned input transducer is a piezoelectric device it may be used as an output device. The composite transducer is encased in an open cell foam to provide: comfort to the person wearing the device, a windscreen for the input transducer, a spacer between the composite transducer and the ear of the person wearing the device for admitting the noise waves directly into the mixing chamber (ear canal), and an absorber for high frequency attenuation.

The open cell foam allows the original acoustic signal to reach the ear by centering the composite transducer over the ear canal so that the original acoustic wave is not blocked entirely. Thus, this same acoustic wave front is received by the input transducer, converted to an electrical signal and processed in the control unit. The processed signal is phase inverted and applied to the output transducer. Since the diaphragms of the input and output transducers are in the same plane, the processed signal output is substantially in the same time domain as the original acoustic wave. That is the original signal and the processed signal are substantially 180 degrees out of phase and cancel in the ear canal. A person skilled in the art will recognize that although the diaphragms of the input and output transducers are in the same plane they both will have independent ballistic characteristics that cause a slight distortion and time delay however, the processed signal output is substantially in the same time domain as the original acoustic wave. Also a very slight delay for the electronics to process the signal exist but again, compared to the speed of sound this is very slight. The high frequency attenuation provided by the open cell foam helps to passively reduce some of the acoustic signal level thereby increasing the efficiency of the apparatus.

BRIEF DESCRIPTION OF THE DRAWINGS

Other features and objects of the invention will become more readily apparent from the following detailed description when read in conjunction with the accompanying drawings in which.

BRIEF DESCRIPTION OF THE PREFERRED EMBODIMENT

Figure 3A:
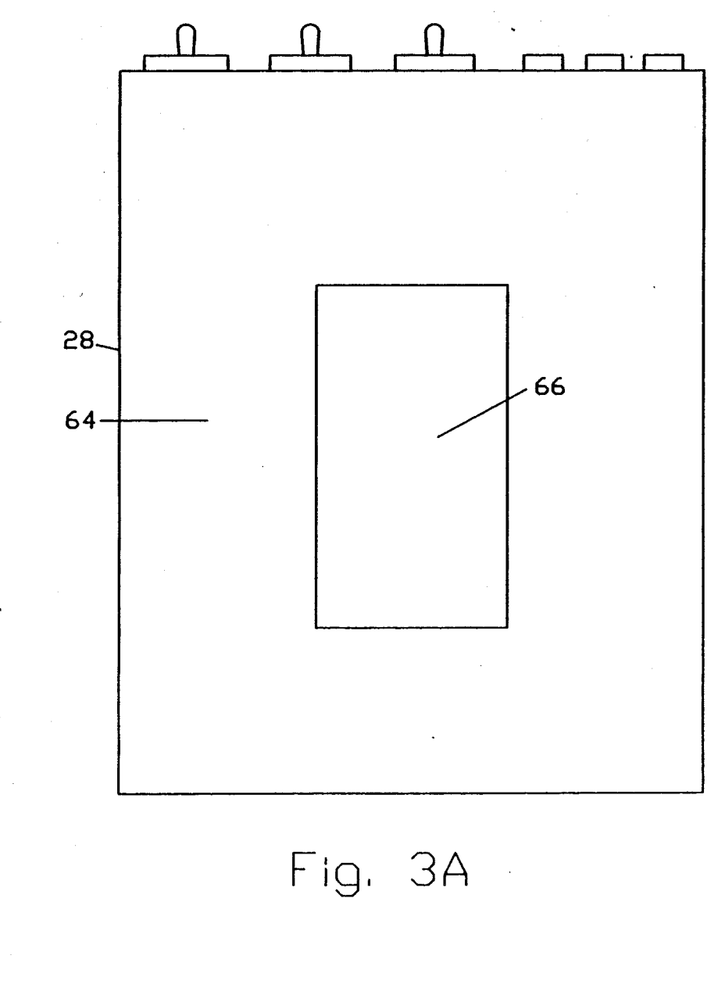
FIGS. 3a-3c are rear, front and top views of the controller.
Figure 3B:
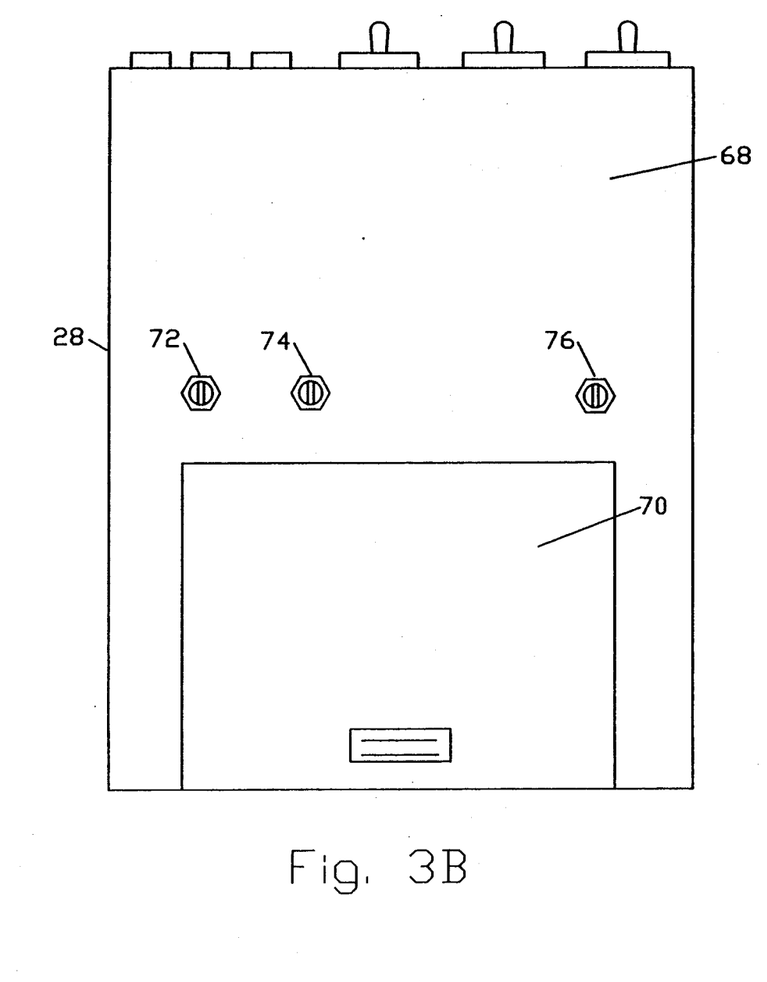
Figure 3C:
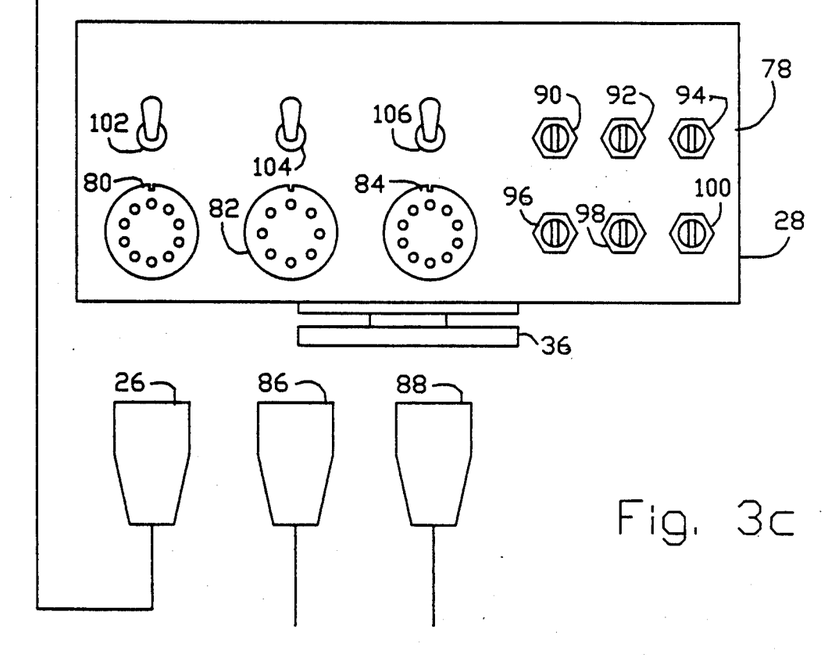

The electroacoustic apparatus 10 (FIG. 1) includes by way of example and not limitation a pair of composite transducer packages 12 and 14 connected to a corresponding pair of attachment blocks 16 and 18 of an adjustable headband 20. Attachment block 18 also attaches a boom microphone 22 to the headband 20. A cable 24 has one end connected to the adjustable headset's composite transducers and an opposing end connected to a male connector 26 for connecting the headset to a controller 28 (FIGS. 3a-3c).

The composite transducers 12 and 14 (FIG. 1) are used to convert the acoustic source signal to an electrical signal and simultaneously convert a processed electrical signal to an acoustic signal. They are encased in blocks of open cell foam material 30 and 32. The composite transducers are designed to be held in place directly over the ear canals by the open cell foam blocks. Thus, the composite transducers do not "plug" the ear, as it is necessary to allow the original sound wave to arrive at the ear canal. The open cell foam blocks 30 and 32 are configured to provide: comfort to the person wearing the apparatus, a windscreen for the composite transducers, a spacer between the composite transducers and the ears of the person wearing the device, and high frequency attenuation. Thus configured, the open cell foam blocks allow the original acoustic signals to reach the ears even though the composite transducer is in place over the ear canal. The attachment block 16 and 18 also serve as paths between the headband and the user's head to assist in the comfort factor of the headset. The adjustable headband is designed so that the wires crossing from one side of the user's head to the other is concealed reducing the risk of damage and aiding in cosmetic appearance. The boom microphone 22 is an optional feature that may be used for additional communication needs. Finally, the controller 28 is configured to allow several functions to be performed as will be described hereinafter.

Figure 1:
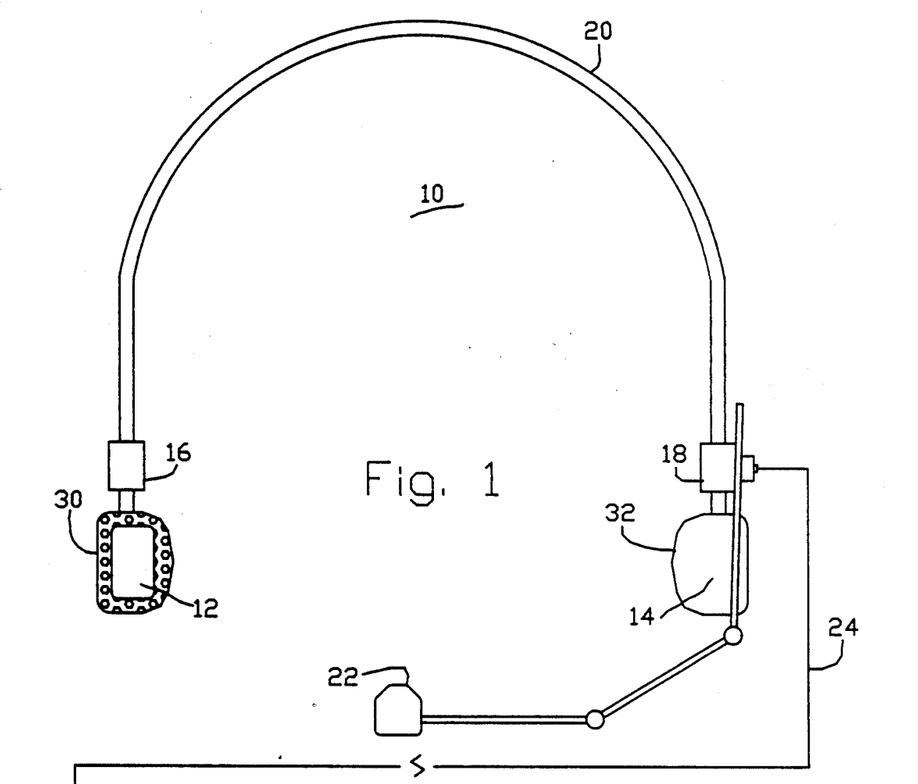
FIG. 1 is a plan view of the multifunction electroacoustic apparatus constituting the subject matter of the invention.

The composite transducers 12 and 14 have for their purpose a solution of the problem of how to receive and convert the original acoustic wave signal to an electrical signal, process it with a 180 degrees phase shift, and convert it back to an acoustic signal so that it can add with the original acoustic wave signal and cancel out all in the real time domain. That is, the phase of all frequencies of the original acoustic wave are added substantially 180 degrees out of phase to substantially cancel the original acoustic wave. The composite transducers 12 and 14 are identical in construction and therefore only one need be described in detail.

The composite transducer (FIGS. 2a-2c) includes an input transducer 34 (FIG. 2a) and an output transducer 36. The input transducer 34 is constructed of a material that is not influenced by a magnetic field. Thus, a suitable input transducer is an electret condenser or a piezoelectric element 38. An input transducer housing 42 and isolation cover 40 along with the magnetic structure 50 hold the input transducer 34 in place and provide isolation between the input transducer 34 and the output transducer 36 to reduce the potential of feedback. An outer housing 46 covers the output transducer diaphragm 44. The output transducer 36 includes a diaphragm or cone 44 which is protected by a snap-on perforated cover 46. A mounting ring 48 holds the outer edge of the output transducer's diaphragm 44 and the snap-on cover 46. A magnet structure 50 is pinned to the mounting ring 48. A coil form 52 for coil windings 54 is attached to the output transducer's diaphragm 44 between its inner and outer peripheries. This coil form holds the winding centered in a gap 56 of the magnetic structure 50 and moves the output diaphragm 44 when a signal is applied to the coil. The output transducers magnetic structure 50 also provides the overstructure for the composite transducer. The magnetic structure has vent ports 58 spaced around the circumference of the structure to relieve back pressure to the output diaphragm 44. Thus, the output transducer 36 is fixed and the input transducer 34 and its housing 42 are moved by a set screw 60 to affect alignment of the input and output transducers diaphragms 38 and 44 in the same plane.

Figures 2A, 2B, 2C:
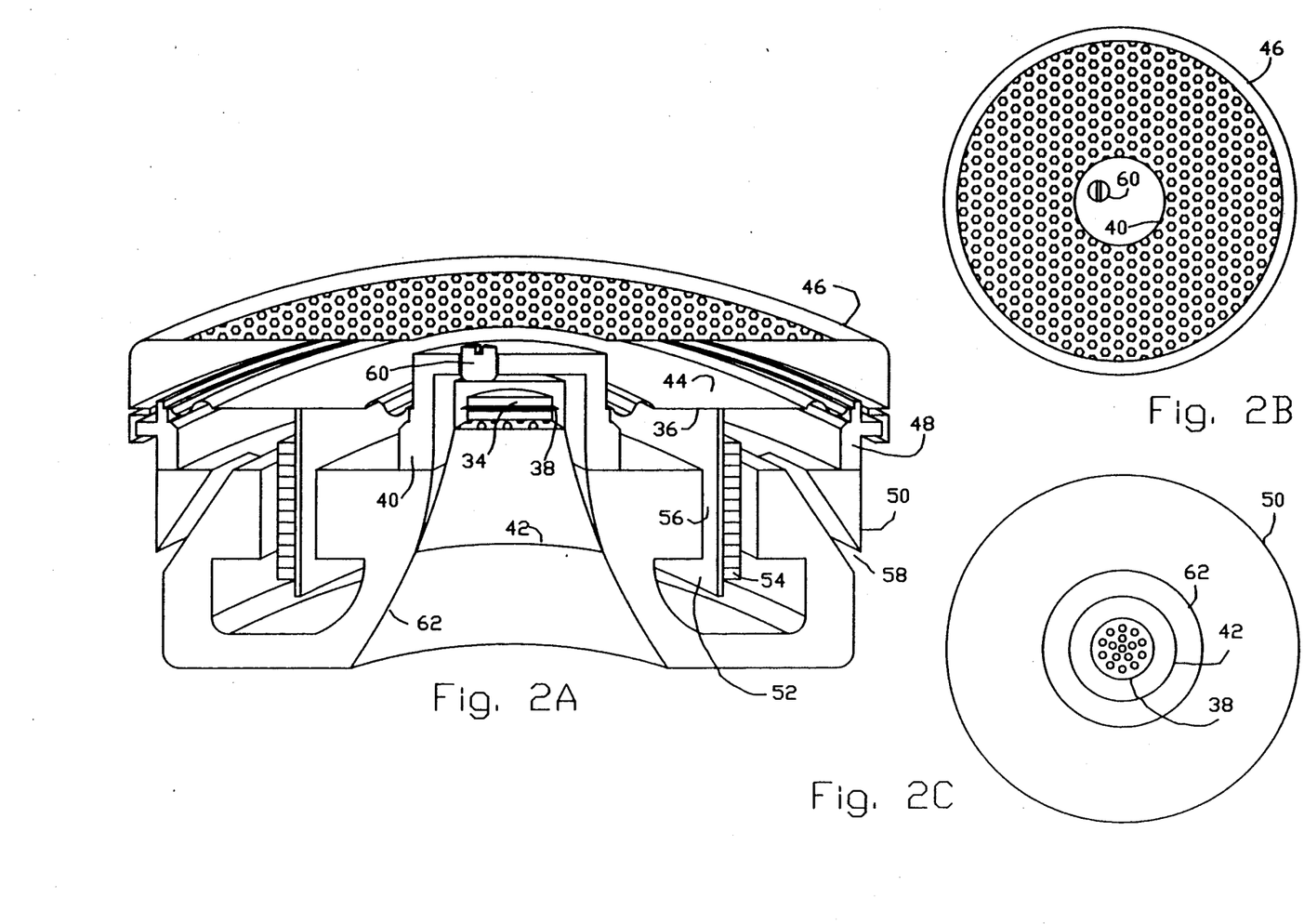
FIGS. 2a-2c are side, front and rear views respectively of the composite transducer.

Thus, the composite transducer may be described as two independent transducers mounted so their diaphragms are oriented in opposite directions, with the input transducer mounted in the middle of the output transducer, and both diaphragms aligned in the same plane. The voice coil for the output transducer is mounted in the middle of the diaphragms which allows the pole piece to be hollowed to allow the mounting of the input transducer therein with its diaphragm in the same plane as the output diaphragm. The housing 40 covers this "hollow pole center" and the input transducer to prevent a direct feedback path between the diaphragms. The set screw 60 in this housing allows fine alignment of the input transducer's diaphragm with the output transducer's diaphragm.

The inside edges of this "hollowed pole center" has smooth conically expanding sides 62 to direct the acoustic signal source to the input diaphragm. This structure may be compared to a conical horn and is used to broaden the frequency range the input transducer can receive and to minimize the resonances and phase distortions caused by waveguides. It will be appreciated by those persons skilled in the art that other style waveguides, by their inherent properties, may be used to signature the received signal for individual applications.

The choice of transducer design is critical when constructing the composite transducer. As the output transducer is a voice coil type device, a magnetic field exists in the area that the input transducer occupies. If the input transducer were of a design similar to a dynamic microphone, the results would not be desirable. The magnetic field of the output transducer's section would interfere with the input section since the magnetic fields would be coupling and opposing in certain regions. Trying to share the same magnet structure for each transducer does not lend itself to aligning the diaphragms in the same plane with one inside the other. Thus, the design used for the input transducer should be of the electret microphone style, a piezo film transducer, or some other style and design that does not rely on a magnetic field that could be altered by the fields generated by the output transducer.

Accordingly, the above described composite transducer reduces to a negligible effect problems associated with the velocity of the acoustic wave, reflections or delays, and phase shift filters.

The control unit 28 (FIGS. 3a–3c) may be made small enough to fit into a pocket, or made to fit a variety of other size chassis. Thus, the backside 64 (FIG. 3a) is provided with the clip 66 in order that the controller may be worn on a belt, or clipped to apparel suitable to support the unit.

The front side 68 (FIG. 3b) of the controller 28 is provided with an access door 70 to a battery power pack compartment. Input transducer output gain adjusters 72 and 74 and a boom microphone gain adjuster 76 are provided on the front side above the access door for adjusting, respectively, the input transducer output gain and boom microphone gain.

The top side 78 (FIG. 3c) of the controller 28 is provided with 3 female type receptors 80, 82 and 84. Receptacle 80 is adapted to receive the mating plug 26 of the headset. The receptacles 82 and 84 are adapted to receive, respectively, a mating connector 86 for connecting an external power input, or an auxiliary signal input, or a boom microphone output, and a mating connector 88 for connecting a composite transducer input or composite transducer output, or a controller signal output.

Standard type gain adjusters 90, 92 and 94 are provided for adjusting, respectively, the headset gain, external input gain, and signal output gain of the left composite transducer 12; while, gain adjusters 96, 98 and 100 are provided for adjusting, respectively, the headset gain, external input gain and signal output gain of the right composite transducer 14.

Three toggle switches 102, 104 and 106 complete the configuration of the top of the controller 28. Toggle switch 102 is provided to control the headset functions and includes reduction, off and amplification positions; toggle switch 104 is provided to control the headset input and includes normal, off and external operation positions; and toggle switch 106 controls the power selection and includes battery, off and external positions.

Figure 4:
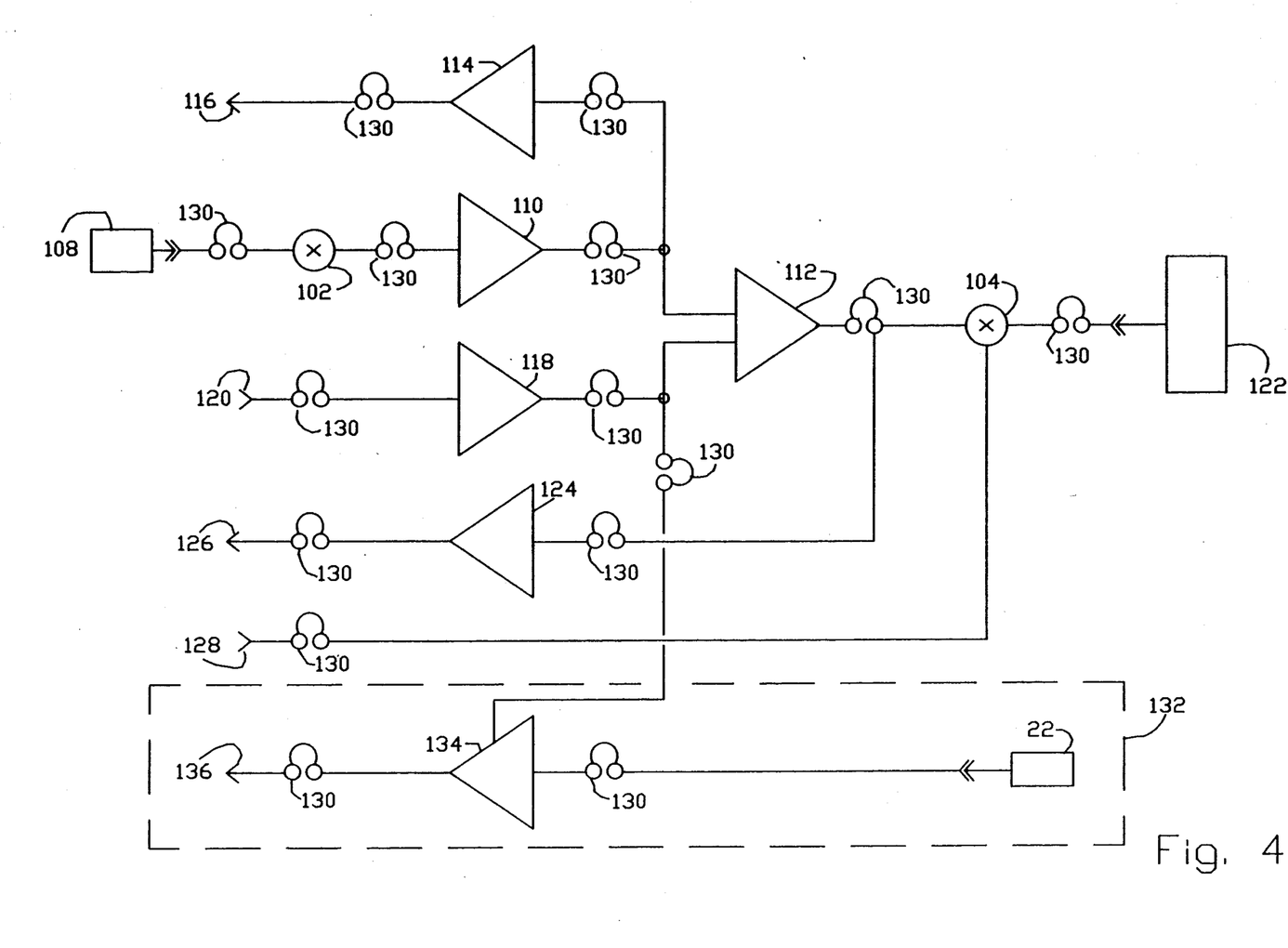
FIG. 4 is a schematic view in block form of the control circuitry.
Figure 5:
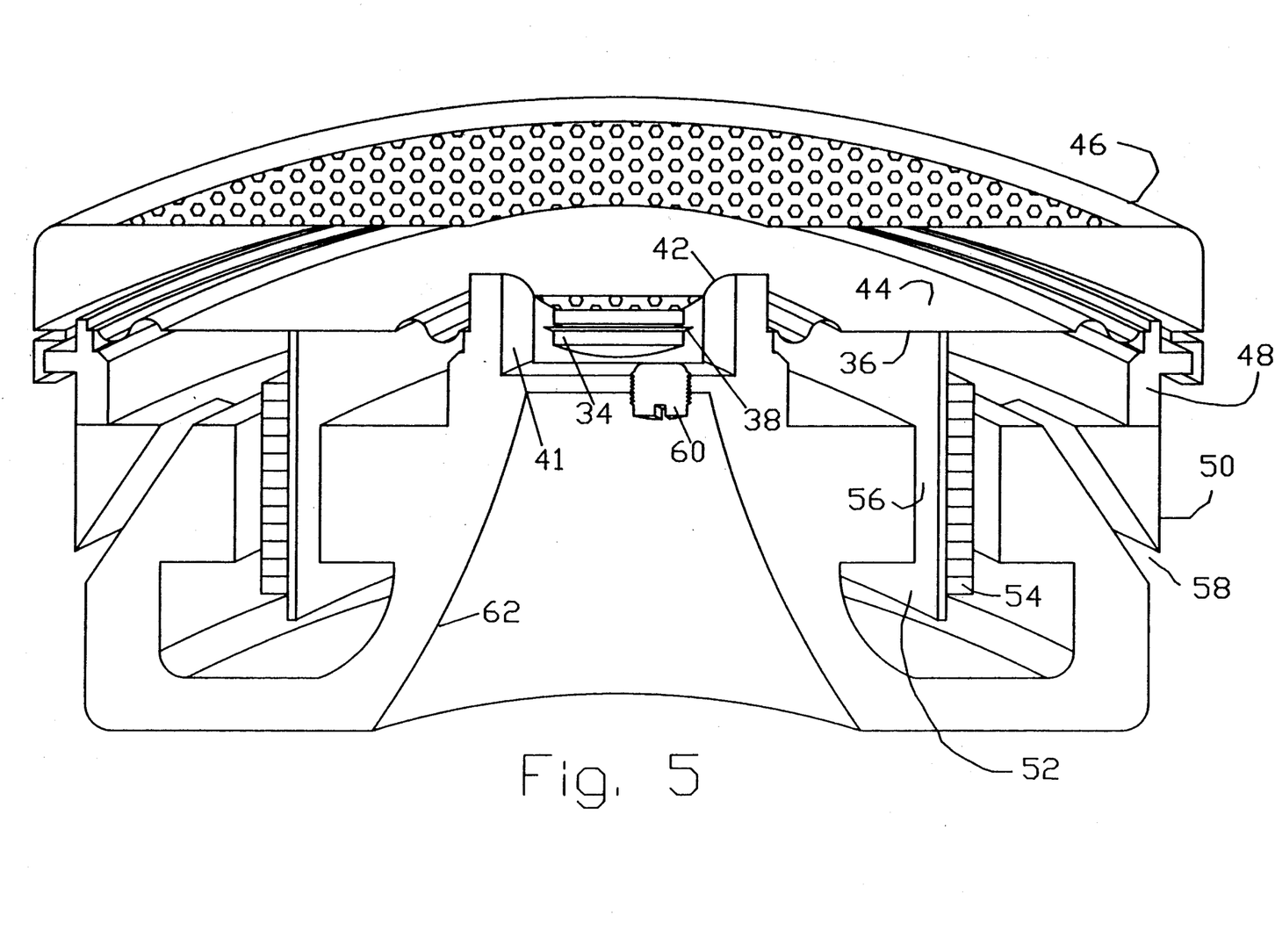
Figure 6:
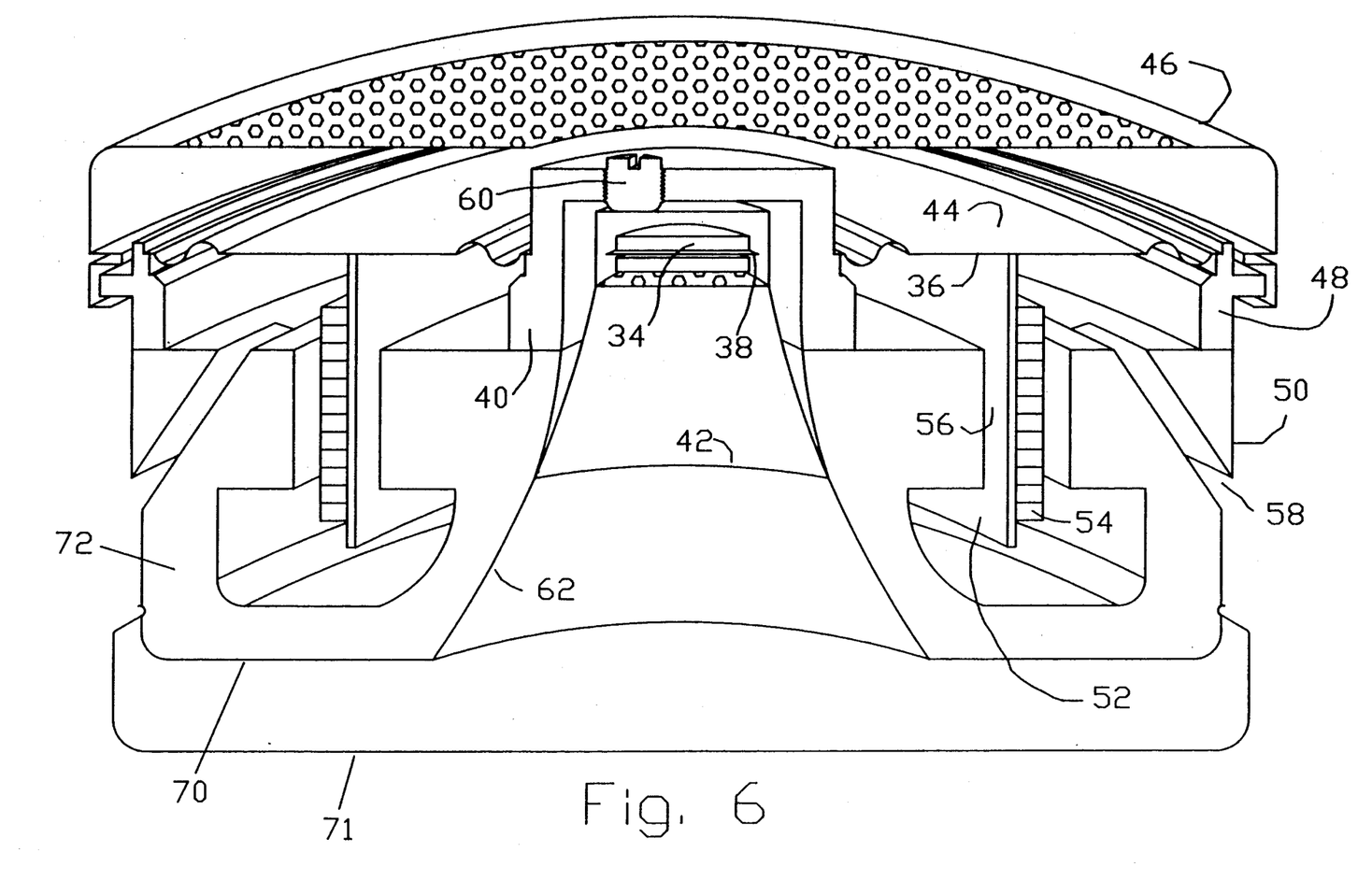

Referring now to FIG. 4 for a description of the controller circuitry for one channel and the boom microphone circuit. The controller circuitry includes an input transducer section 108 of the composite transducer which converts the acoustic source signal to an electrical signal for processing. The headset function switch 102 is connected to the input section 108 to control the input transducer input to a transducer preamplifier 110. Switch 102 is a three-positioned switch used to select one of the following three functions:

1. The inverted phase for cancellation (reduction);
2. the normal phase for signal amplification; and
3. to cut off the input transducer.

The transducer preamplifier 110 is connected to the junction of the inverted terminal of an operational amplifier (Op. Amp.) 112 serving as a mixer/output transducer amplifier and to an operational amplifier 114. Operational amplifier 114 has its output connected to an input transducer output connector 116. The noninverting terminal of the operational amplifier 112 is connected to the output of an auxiliary input instrumentation preamplifier 118 having its input terminal connected to an auxiliary input connector 120 for inputting a signal to the auxiliary input instrumentation preamp 118 to the Op. Amp. 112. The headset input switch 104 selects between the output of the mixer/output transducer (Op. Amp.) 112 or the output transducer direct input 128 for output to the output section of the composite transducer 122. The mixer/output transducer (Op. Amp.) 112 is buffered by (Op. Amp.) 124 for isolation and gain control to provide the controller generated signal to be output to connector 126.

An input connector 128 is connected to the switch 104 for inputting a signal to the transducer section 122. This input connector is used to allow the electroacoustic apparatus 10 to be used as a normal set of headphones.

The circuit is replete with patch points 130 for the addition of subcircuits or circuit components; for example, the transducer preamp 110 has a patch point for the addition of filters and/or phase shift circuits to provide a select narrow band noise cancellation if desired. Because of the design of the composite transducer, these circuits are not needed or used for broadband noise cancellation.

The optional boom microphone circuit 132 includes the boom microphone 22 which is connected by connector 26 to a preamplifier 134 for amplifying the signal output of the boom microphone to a working level. The output of the optional boom mike preamp 134 is mixed with the output of the aux input preamp 118 and feed to the noninverting input of mixer/output transducer (Op. Amp.) 112. This provides a side tone signal to the operator of the signal from the boom microphone.

The operations of the electroacoustic apparatus 10, which is to provide each of the above mentioned useful tools for the ear and its hearing needs, are as follows:

1. For a device to reduce the sound level to the ears giving audible noise reduction the headset function switch 102 and the output transducer input section select switch are set, respectively, to the "Reduction" and "Normal" positions. Thus, an acoustic wave is detected and converted to electrical wave energy signals by the transducer input section 108 and fed to the phase selection switch 102. The switch 102, being positioned in the "Reduction" position, passes the electrical signals to an inverting input of the linear phase and gain instrumentation amplifier 110. After the signal has been inverted and amplified, it is fed to the mixer/amplifier (Op. Amp.) 112 that, in turn, delivers the amplified electrical signals to the selection switch 104 which being set to the "Normal" position passes the amplified electrical signals to the output transducer section 122.

The level that is outputted by the output section 122 of the composite transducer must be adjusted to match the level of the original signal in the ear canal. The individual level (gain) controls 90-94 and 96-100 are used to adjust the gain for the left and right ears, respectively. This is necessary because not everyone's ears are identical to each other or to anyone elses ear. Thus, maximum reduction is achieved by adjusting the gain until the signal heard by the ear has reached its minimum level and any more gain causes the signal to increase in gain.

2. For a device to perform a hearing aid function, such as amplifying the sound level to the ears, the apparatus can amplify a signal using two methods. The first method uses the exact same components and circuitry described above for use when reducing the signal level. The difference is that instead of adjusting the gain to maximize the reduction, the gain is increased beyond the point of minimum level heard by the ear to a desired level or the maximum level before feedback occurs between the input and output sections of the composite transducer. The second method uses the same components and circuitry except the phase or headset function switch 102 is set to the "Amplification" position. The difference in this setting is that the input transducer signal is not fed to the noninverting input of the instrumentation amplifier 102, and the gain of the system is adjusted to the desired level below feedback.

3. For a device to provide a communication interface for inputting special signals such as dispatched or emergency communications and providing a signal output from a boom microphone while using one of the desired functions of the apparatus such as its noise reduction capabilities, the apparatus will accept an external signal presented to the auxiliary input 120. This signal is fed to the Op. Amp. 118 to adjust the gain on the signal and to match impedances. The signal then goes to the mixer/output transducer amplifier 112 where it is summed with a signal presented by the input transducer amplifier 110. This summed signal is then passed to the output transducer input select or "Headset Input" switch 104. For boom microphone operation, the boom microphone 22 message signals are amplified by the preamplifier 134 and the resultant signal is presented to the output connector 136. An external device connected to the output connector 136 receives the resultant signal.

4. For an amplified headset device to be used with personal entertainment equipment or where other amplified signals are required to drive a miniature type headset, the headset function switch 102 is set to the "Off" position and the auxiliary input 120 is used. The "Off" setting of switch 102 prohibits any signal except the auxiliary input from being amplified and presented to the output transducer input select or "Headset Input" switch 104. The boom microphone would not normally be used in this mode of operation, but may be if needed to perform a special function such as an entertainer using the headset as a monitor and the boom microphone for singing or speaking.

5. For a signal source to feed personal or professional recording devices such as mono or binaural microphone sources, the apparatus will pass a signal from the input transducer sections 108 of the composite transducers mounted on the headset to the additional Op. Amp. 114 which isolates the output of the transducer preamp 110 from an input to a device such as a recorder that may be connected to the connector 116.

6. For a normal open air ultralight headphone for use in anyway that such a type headphone may be used, the output section 112 of the composite transducer is accessed directly by setting the output transducer input select or "Headset Input" switch 104 to its "External" position. This presents to the output transducers section 122 of the composite transducer the signal fed to the connector 128. Thus, except for the switch 104, no other internal circuitry is used.

Although only a single embodiment of this invention has been described, it will apparent to a person skilled in the art that various modifications to the details of construction shown and described may be made without departing from the scope of this invention.

What is claimed is:

1. An electroacoustic apparatus for performing multiple electroacoustic functions for the human ear and its hearing needs comprising:

a composite transducer means including an input transducer means for converting received sound waves to corresponding electrical signals, an output transducer means for converting processed electrical signals to corresponding sound waves for input into a mixing means, said input transducer means and output transducer means being operatively aligned in the same plane for positioning the input transducer means close to the mixing means for receiving substantially the same received sound waves including any reflections received by the mixing means and a support means connected to the composite transducer means for supporting the composite transducer means in a selected position for receiving a portion of the received sound waves and for passing a portion of the received sound waves to the mixing means; and a control means including a circuit having an input means connected to the input transducer means for receiving selectively the electrical signals, a phase inverter means connected to the input means for inverting the phase of the received electrical signals, and an output means connected to the output transducer means for selectively outputting the inverted electrical signals to the output transducer means, said output transducer means being substantially aligned in the same plane of the input transducer means for generating processed sound waves corresponding to the received sound waves but 180 degrees out of phase with respect thereto for arrival at the mixing means at the same time the received sound waves arrive at the mixing means for substantial cancellation;

wherein the control means input means includes a function selection means connected to the input transducer means for controlling the connection of the output of the input transducer means to the phase inverter means.

2. An electroacoustic apparatus according to claim 1 further comprising a headset including a headband and the composite transducer means, said composite transducer means being connected to the headband, and wherein the control means is mounted in a container and includes an electrical connector means for remotely connecting the control means to the composite transducer means.

3. An electroacoustic apparatus according to claim 2, wherein the headset further includes a boom microphone, and the circuit of the control means further includes a preamplifier means connected to the boom microphone for amplifying the output of the boom microphone, an auxiliary circuit input means for connecting the output of the preamplifier to the phase inverter means, and an output circuit means connected to the output of the phase inverter means for outputting a signal to an external device.

4. An electroacoustic apparatus according to claim 1 wherein the function selection means includes a switch having "Reduction", "Off" and "Amplification" positions for controlling the input of the input transducer means, respectively, for sound cancellation, for opening the circuit between the input transducer means and phase inverter means, and for sound amplification.

5. An electroacoustic apparatus according to claim 1, wherein the control means' output means includes an input selection means connected to the output transducer means for controlling the connection of the output of the phase inverter means to the output transducer means.

6. An electroacoustic apparatus according to claim 4 wherein the input selection means includes a switch having "Normal", "Off" and "External" positions for controlling inputs to the output transducer means, respectively, for sound cancellation, for opening the circuit between the phase inverter means and the output transducer means, and for connecting the electrical output of another device directly to the output transducer means for headphone use.

7. An electroacoustic apparatus according to claim 1 wherein the phase inverter means includes a transducer preamplifier connected to the input transducer means for preamplifying the input transducer means electrical signal output, and a mixer/output transducer operational amplifier having a phase inverter terminal connected to the transducer preamplifier for inverting the phase of the electrical output of the preamplifier.

8. An electroacoustic apparatus according to claim 7 wherein the control means further includes an input transducer output line driver circuit means connected to the output of the transducer preamplifier for outputting a signal from the input transducer means to a device which is responsive thereto, said input transducer output circuit means including means for isolating the output of the transducer preamplifier from the signal input to the device.

9. An electroacoustic apparatus according to claim 7 wherein the control means further includes an auxiliary device connecting circuit means connected to a noninverting terminal of the mixer/output transducer operational amplifier for summing output signals of an auxiliary device with any signals received from the input transducer means, said auxiliary device connecting circuit means including an operational amplifier for adjusting the gain on the incoming signals and for matching impedances.

10. An electroacoustic apparatus according to claim 9 wherein the control means further includes a line driver circuit means connected to the mixer/output transducer operational amplifier for outputting the signal thereof for use as needed.

11. An electroacoustic apparatus according to claim 1 wherein the control means further includes an individual gain level control means for adjusting the signal output gain of the composite transducer whereby for maximum reduction the gain is adjusted until the signal heard by the ear reaches its minimum level, and for amplification the gain is increased beyond the point of minimum level heard by the ear to a desired level.

12. An electroacoustic apparatus for performing multiple electroacoustic functions for the human ear and its hearing needs comprising:

a composite transducer means adapted to be mounted adjacent a human ear including an input transducer means for converting received sound waves to corresponding electrical signals, an output transducer means for converting processed electrical signals to corresponding sound waves for input into a mixing means, means for connecting said input transducer means and output transducer means in substantially the same plane normal to the received sound waves for positioning the input transducer means close to the mixing means for receiving substantially the same received sound waves including any reflections received by the mixing means and a support means connected to the composite transducer means for supporting the composite transducer means in a selected position for receiving a portion of the received sound waves and for passing a portion of the received sound waves to the mixing means; and a control means including a circuit having an input means connected to the input transducer means for receiving selectively the electrical signals, a phase inverter means connected to the input means for inverting the phase of the received electrical signals and an output means connected to the output transducer means for selectively outputting the inverted electrical signals to the output transducer means, said output transducer means being in operative alignment witht he input transducer means for generating processed sound waves corresponding to the received sound waves but substantially 180 degrees out of phase with respect thereto for arrival at the mixing means at the same time the received sound waves arrive at the mixing means for substantial cancellation.

13. An electroacoustic composite transducer apparatus for use in electroacoustic devices comprising:

an input transducer and an output transducer, said input and output transducers having diaphragms oriented in opposite directions;

an electric coil; and a transducer frame having a hollow pole piece and an exterior electric coil support means, said input transducer being mounted in the hollow pole piece with its diaphragm oriented in a direction for receiving incoming sound waves and generating electrical signals corresponding to the incoming sound waves and having output leads for connecting the electrical signals to a control means for processing, and said output transducer being mounted outside the hollow pole piece with its diaphragm positioned in substantially the same plane of the input transducer's diaphragm and having a portion between its peripheral edges in engagement with the electric coil support means, said electric coil having leads for connection to the control means for receiving the processed electrical signals for driving in real time the output transducer's diaphragm for outputting sound signals corresponding to the processed electrical signals of the control means 14. An electroacoustic composite transducer apparatus according to claim 13 wherein the transducer frame further includes a housing for covering the hollow pole piece and the input transducer to prevent a direct feedback path between the diaphragms of the input and output transducers.

15. An electroacoustic composite transducer means according to claim 14 wherein the housing includes an input transducer position adjustment means for aligning the input transducer's diaphragm in the plane of the output transducer's diaphragm.

16. An electroacoustic composite transducer means according to claim 13 wherein the hollow pole piece has conically expanding sides for directing acoustic signals to the input transducer's diaphragm whereby the frequency range that the input transducer can receive is broadened, and resonances and distortions are minimized.

17. An electroacoustic composite transducer means according to claim 13 wherein the input transducer is a nonmagnetic field type transducer.

18. An electroacoustic composite transducer means according to claim 17 wherein the input transducer is selected from a nonmagnetic field type group consisting of an electret type and a piezoelectric type.

19. An electroacoustic composite transducer according to claim 13 further including an encasement means for encasing the input and output transducers for providing comfort to one wearing the electroacoustic apparatus, a wind screen for the input transducer, a spacer for centering the input and output transducers with respect to the encasement means and allowing a portion of the acoustic wave to pass around the input and output transducers and for high frequency attenuation.

20. An electroacoustic composite transducer means according to claim 19 wherein the encasement means comprises an open cell foam.

21. An electroacoustic device for cancelling sound waves in a bounded ear canal, comprising:

an input transducer for converting sound waves incident on a pickup surface of the input transducer into corresponding input electrical signals;

an output transducer for converting output electrical signals into corresponding sound waves which emanate from a diaphragm surface of the output transducer into said bounded ear canal, said output transducer defining a boundary of said bounded ear canal;

a transducer frame to which said input transducer and said output transducer are fixed so that said pickup surface of said input transducer and said diaphragm surface of said output transducer are in substantially the same plane, the input transducer and the output transducer being independently mounted on the transducer frame such that the movement of the pickup surface relative to the transducer frame is primarily in response to incident sound waves, said transducer frame defining another boundary of said bounded ear canal; and a control means for receiving the electrical signals from the input transducer and for generating the output electrical signals to the output transducer, the output electrical signals being substantially 180 degrees out of phase with respect to said sound waves incident on said pickup surface of said input transducer so that sound waves in said bounded ear canal are cancelled.

22. The electroacoustic device of claim 21 wherein said pickup surface of said input transducer is external to said boundary, is of said bounded ear canal and wherein said pickup surface faces away from said bounded ear canal, said incident sound waves being incident on said pickup surface from outside said bounded ear canal.

23. The electroacoustic device of claim 21 or 22 wherein said output transducer surrounds said input transducer in said same plane.

24. The electroacoustic device of claim 23 wherein said diaphragm surface of said output transducer is defined by the area between two concentric circles of unequal diameter in said same plane, said input transducer being located within the area bounded by the concentric circle with the smaller diameter.

25. The electroacoustic device of claim 23 furhter comprising an adjustent means for adjusting the position between said pickup surface of said input transducer relative to said same plane.

26. The electoracoustic device of claim 23 further comprising an adjustment means for adjusting the relative position between said diaphragm surface of said output transducer and said pickup surface of said input transducer.

27. The electoacoustic device of claim 21 wherein said control means utilizes the negative feedback input of an operational amplifier to invert said input electrical signals to generate said output electrical signals with minimal hardware.

28. The electroacoustic device of claim 21 wherein said input transducer is a nonmagnetic field type transducer and wherein said diaphragm surface of said output transducer is moved via an electrical coil.

29. The electroacoustic device of claim 21 wherein the control means further comprises an individual gain level control means for adjusting the amplitude of the output electrical signals, whereby a maximum reduction in gain is achieved by adjusting the individual gain level control means until the signal heard by the ear reaches its minimum level, and whereby amplification in gain is achieved by adjusting the individual gain level control means beyond the point of said minimum level until the signal heard by the ear achieves a desired amplified level.

* * * * *